United States Patent
Couturier et al.

(10) Patent No.: US 10,515,525 B2
(45) Date of Patent: Dec. 24, 2019

(54) METHOD FOR MONITORING THE OPENING OF A CONTAINER

(71) Applicant: Safran Electronics & Defense, Boulogne Billancourt (FR)

(72) Inventors: Emmanuel Couturier, Boulogne Billancourt (FR); Nicolas Fanton, Boulogne Billancourt (FR); Pierre-Jean Tine, Boulogne Billancourt (FR)

(73) Assignee: SAFRAN ELECTRONICS & DEFENSE, Boulogne Billancourt (FR)

( * ) Notice: Subject to any disclaimer, the term of this patent is extended or adjusted under 35 U.S.C. 154(b) by 0 days.

(21) Appl. No.: 16/314,038

(22) PCT Filed: Jun. 28, 2017

(86) PCT No.: PCT/EP2017/066062
§ 371 (c)(1),
(2) Date: Dec. 28, 2018

(87) PCT Pub. No.: WO2018/002180
PCT Pub. Date: Jan. 4, 2018

(65) Prior Publication Data
US 2019/0325718 A1    Oct. 24, 2019

(30) Foreign Application Priority Data
Jun. 30, 2016    (FR) .................................... 16 56251

(51) Int. Cl.
*G08B 13/08*    (2006.01)
*G08B 25/10*    (2006.01)
*G16H 40/20*    (2018.01)

(52) U.S. Cl.
CPC ............. *G08B 13/08* (2013.01); *G08B 25/10* (2013.01); *G16H 40/20* (2018.01)

(58) Field of Classification Search
CPC ......... G08B 13/08; G08B 25/10; G16H 40/20
See application file for complete search history.

(56) References Cited

U.S. PATENT DOCUMENTS

| 7,061,377 | B1 | 6/2006 | Kraus | |
| 8,115,609 | B2 * | 2/2012 | Ketari | ................ G08B 13/1427 340/426.16 |
| 9,323,894 | B2 * | 4/2016 | Kiani | ..................... G08B 21/24 |

(Continued)

*Primary Examiner* — Mohamed Barakat
(74) *Attorney, Agent, or Firm* — Muncy, Geissler, Olds & Lowe, P.C.

(57) ABSTRACT

A method of monitoring the opening of a container, the method comprising the steps of:
putting a monitoring device into a closed mode of operation (11) when detection means detect that the container is closed, in which mode a communications module sends closed messages at a first status repetition rate;
when the detection means detect that the container is open, putting the monitoring device into a warning mode of operation (12) in which the communications module sends open messages at a second status repetition rate; and
when the monitoring device is in the warning mode of operation (12) and the communications module receives an opening validated message, putting the monitoring device in an opening validated mode of operation (13) in which the communications module sends open messages at a third status repetition rate.

7 Claims, 3 Drawing Sheets

(56) References Cited

U.S. PATENT DOCUMENTS

| | | | |
|---|---|---|---|
| 9,916,743 B2* | 3/2018 | Harrison | E05B 83/10 |
| 10,140,834 B2* | 11/2018 | Barcala | G06F 1/3209 |
| 2006/0055533 A1 | 3/2006 | Kirkland et al. | |
| 2010/0302025 A1* | 12/2010 | Script | G01P 15/09 |
| | | | 340/539.1 |
| 2013/0076513 A1* | 3/2013 | Eskildsen | G08B 13/08 |
| | | | 340/565 |
| 2015/0039267 A1 | 2/2015 | Busch et al. | |

* cited by examiner

METHOD FOR MONITORING THE OPENING OF A CONTAINER

The invention relates to the field of monitoring the opening of containers.

BACKGROUND OF THE INVENTION

Most industrial products or valuable goods are, at some time or another, stored in some kind of container for transport, storage, or confinement purposes.

The term "container" is used herein to mean any type of box, package, frame, storage space of any kind (e.g. an empty space in an aircraft, in a ship, in a truck, in a rail car, etc.), that is defined by an enclosure having access means that can be open or closed (e.g. a lid, a door, a hatch, etc.).

Naturally, it is fundamental to be able to monitor the opening of such a container, in particular in order to avoid or to detect the occurrence of theft or of a fraudulent manipulation, or indeed to be able to avoid or to detect an anomaly in the operation of the means for accessing the container.

For this purpose, certain containers include a numbered metal rod (or "seal"). While a container is being transported, the seal is put into place prior to departure of the container so as to prevent the container being opened. On receiving the container, it is verified that the number on the seal corresponds to the number of the seal that was put into place before the departure of the container, and the seal is cut so as to end transport of the container and give access to the object stored inside the container. That solution is reliable and inexpensive, but it is essentially manual. In addition, after opening, when it is only a portion of the contents of the container that is taken out, and it is desired to prevent theft of the remaining portion, then the container needs to be reclosed and a new seal installed.

Certain containers are thus provided with electrical monitoring devices. Electrical monitoring devices are either connected by a wired connection to an external source of electricity (e.g. mains), thereby making them more complex to use, or else they are themselves independently powered.

Independent power is difficult to implement since it is then necessary to ensure that monitoring is effective while also limiting the electricity consumption of electrical monitoring devices so that they can remain independent throughout the time taken for transport.

OBJECT OF THE INVENTION

An object of the invention is to monitor the opening of a container by means of a monitoring device that presents low electricity consumption.

SUMMARY OF THE INVENTION

In order to achieve this object, there is provided a monitoring method for monitoring the opening of a container, the monitoring method being performed by a monitoring device comprising means for detecting opening and closing of the container and a communications module, the monitoring method comprising the steps of:
  putting the monitoring device into a closed mode of operation when the detection means detect that the container is closed, in which mode the communications module sends closed messages at a first status repetition rate, the closed messages indicating that the detection means detect that the container is closed;
  when the monitoring device is in the closed mode of operation and the detection means detect opening of the container, putting the monitoring device into a warning mode of operation in which the communications module sends open messages at a second status repetition rate, the open messages indicating that the detection means detect that the container is open; and
  when the monitoring device is in the warning mode of operation and the communications module receives an opening validated message indicating that opening of the container has been validated, putting the monitoring device in an opening validated mode of operation in which the communications module sends open messages at a third status repetition rate, the open messages indicating that the detection means detect that the container is open.

Certain situations require the monitoring of opening the container and the sending of open messages or closed messages to be performed at a high repetition rate, whereas other situations are compatible with monitoring and sending messages at a much lower repetition rate (in particular when opening has been validated by a final addressee of the container). The monitoring method of the invention makes it possible to vary this repetition rate as a function of the situation, and thus to reduce the electrical power consumption of the monitoring device.

The invention can be better understood in the light of the following description of particular, non-limiting implementations of the invention.

BRIEF DESCRIPTION OF THE DRAWINGS

Reference is made to the accompanying drawings, in which.

DETAILED DESCRIPTION OF THE INVENTION

The monitoring method in a first implementation of the invention is used for monitoring the opening of a door 1 of a container 2 containing an object and stored in a depot.

The monitoring method of the invention is performed by a monitoring device fitted to the container 2 and positioned on the container 2.

The monitoring device includes means for detecting opening and closing of the door 1 of the container 2, a microcontroller, a battery, sensors for supervising the status of the monitoring device, a memory, and a communications module.

Figure 1A:
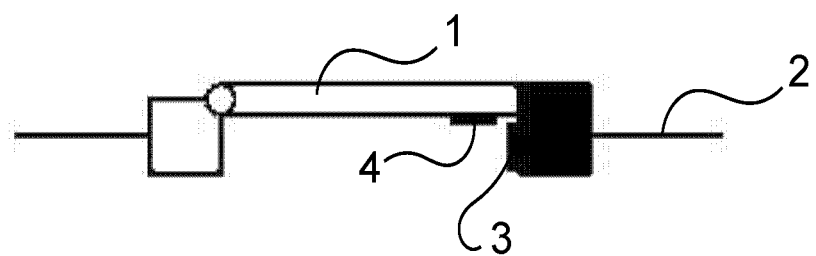
FIG. 1a shows the detection means of a monitoring device when the container is closed.
Figure 1B:
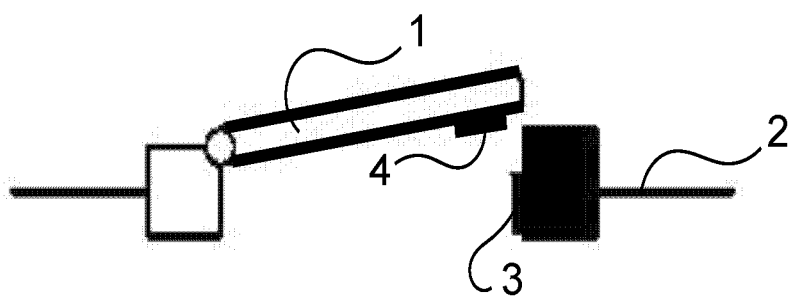
FIG. 1b shows the detection means of a monitoring device when the container is open.

With reference to FIGS. 1a and 1b, the detection means comprise a Hall effect sensor 3 situated on the container 2. The door 1 of the container 2 includes a magnet 4 that generates a magnetic field.

While the door 1 of the container 2 is closed, as shown in FIG. 1a, the magnet 4 of the door 1 is positioned in the immediate proximity of the Hall effect sensor 3, which detects the magnetic field generated by the magnet 4, and which therefore detects that the door 1 is closed.

When the door 1 of the container 2 is open, as shown in FIG. 1b, the magnet 4 of the door 1 is moved away from the Hall effect sensor 3, which does not detect the magnetic field generated by the magnet 4, and which therefore detects that the door 1 is open.

The microcontroller, which is connected to the Hall effect sensor 3, thus receives information as to whether the door 1 of the container 2 is open or closed (and thus whether the container 2 is open or closed).

The detection means also include a first reed switch that is normally open, and a second reed switch that is normally closed, the switches being situated on the container 2 in the proximity of the magnet when the door 1 is closed. The first reed switch and the second reed switch are connected to the microcontroller.

The microcontroller thus keeps a closing count that is incremented on each occasion the first reed switch is closed and thus the door 1 is closed, and an opening count that is incremented on each occasion the second reed switch is closed, and thus the door 1 is open.

The microcontroller detects that the door 4 is open when the values of the opening and closing counts are equal, and that the door 4 is closed when the values of the opening and closing counts are equal. The microcontroller thus validates detection of opening or closing of the door 4 as performed by the Hall effect sensor.

The microcontroller also controls the operation of the monitoring device.

The battery provides the exclusive sources of electricity for powering the entire monitoring device, which is thus powered independently (and which is not connected by a wired connection to any external source of electricity).

The sensors supervising the status of the monitoring device measure internal electrical parameters of the monitoring device in order to monitor both correct operation, and also the remaining capacity of the battery.

The memory serves to store a certain amount of data, and in particular data identifying the monitoring device, the container 2, and the object stored in the container 2, and a certain number of "open" or "closed" statuses of the container 2 as detected by the monitoring device, the internal electrical parameters, the remaining capacity of the battery, the duration(s) of one or more open periods (during which the container 2 remains continuously open), the duration(s) of one or more closed periods (during which the container 2 remains continuously closed), and various other parameters that are stored or calculated by the microcontroller.

The communications module of the container 2 includes an antenna and a radio transceiver. The communications module of the container 2 together with an external communications unit (and possibly together with communications modules of other containers stored in the proximity of the above-mentioned container 2) form a low power wide area network (LPWAN) using technology that has been deigned for the field of the Internet of things (IoT). The technology used in this example is of the narrow band type or of the ultra-narrow band (UNB) type, e.g. LoRa or SigFox.

The communications module thus consumes little electricity. The data rate of communications set up by the communications module is also relatively low, and the messages that are transmitted are relatively small in size (typically twelve bytes), however the data rate and message size are nevertheless sufficient for the presently-intended application.

The communications module is adapted to communicate with the external communications unit in bidirectional manner via the LPWAN network. The communications module is suitable for sending any type of data to the external communications unit, and in particular the data stored in the memory of the monitoring device.

The external communications unit, which is situated in the depot where the container 2 is stored, is itself connected to a server that, in this example, is managed by the final addressee of the object stored in the container 2. Naturally, the server could perfectly well be managed by a party other than the final addressee: the manufacturer of the object, the management of the depot, the transporter, a maintenance manager, etc.

The final addressee can thus be informed at all times and anywhere in the world about the open or closed status of the container 2 and about the proper operation of the monitoring device (naturally providing the container 2 is at a distance from the external communications unit that is compatible with operation of the LPWAN network).

It should be observed at this point that the monitoring device is in a standby mode for most of the time, with the exception of short durations during which it needs to perform the functions of detection, measurement, sending a message, or receiving a message.

The standby mode is a low consumption mode, in which the communications module is deactivated as are most of the components of the monitoring device (with the particular exception of a counter of the microcontroller that is used for waking up the monitoring device).

It should also be observed that the various repetition rates that are mentioned below do not correspond to the repetition rate used for communicating in the LPWAN network (e.g. equal to 2.4 gigahertz (GHz)), but to the repetition rate at which the monitoring device leaves the standby mode in order to perform the functions of detection, measurement, sending a message, or receiving a message.

Figure 2:
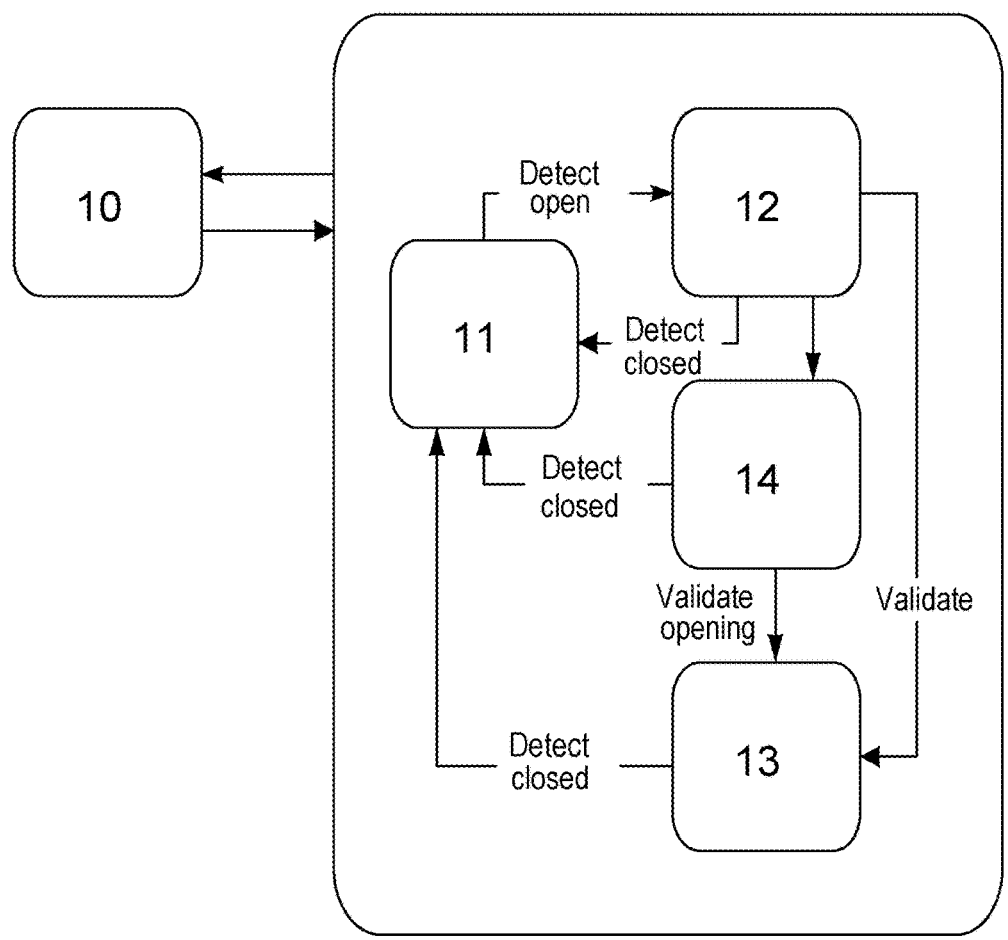
FIG. 2 is a diagram showing the operation of the monitoring method in a first implementation of the invention.

With reference to FIG. 2, there follows a description of the operation of the monitoring method of the invention.

When the monitoring device is switched on, the monitoring device leaves its standby mode 10 and is put by default into a closed mode of operation 11 by the microcontroller.

In the closed mode of operation 11, the detection means detect whether the container 2 is open or closed, the sensors measure the internal electrical parameters of the monitoring device, together with the remaining capacity of the battery, and the communications module sends a first number of status messages at a first status repetition rate.

In this example, the first status repetition rate is equal to sending once per day.

The status messages comprise closed messages indicating that the detection means detect that the container 2 is closed (it being assumed by default that the container 2 is closed), and also information about openings that have not been followed by receiving acknowledgment messages (it is explained below what constitutes the acknowledgment messages).

The communications module also sends a first number of supervision messages at a first supervision repetition rate, which messages comprise the internal electrical parameters of the monitoring device for the purpose of monitoring that it is operating correctly.

The communications module also sends a certain number of capacity messages at a capacity repetition rate, these messages comprising the remaining capacity of the battery, together with an end-of-battery life warning message if the remaining capacity of the battery is below a predetermined capacity threshold.

When the detection means detect that the container 2 is open, the monitoring device is put into a warning mode of operation 12 by the microcontroller.

In the warning mode of operation 12, the detection means detect whether the container 2 is open or closed, the sensors measure the internal electrical parameters of the monitoring device, and the communications module sends a second number of status messages at a second status repetition rate.

The second status repetition rate is higher than the first status repetition rate, and in this example is equal to sending once every ten seconds.

The second number of status messages is higher than the first number of status messages.

The status messages comprise open messages indicating that the detection means detect that the container 2 is open.

The communications module also sends a second number of supervision messages at a second supervision repetition rate, the supervision messages comprising the internal electrical parameters of the monitoring device.

The communications module also "listens" to the LPWAN network by activating the transceiver to receive at a first reception repetition rate.

When the monitoring device is in the warning mode of operation 12 and the detection means detect that the container 2 is closed, the monitoring device is put into the closed mode of operation 11.

When the monitoring device is in the warning mode of operation 12 and the communications module receives an opening validated message meaning that the opening of the container 2 has been validated by the final addressee, the monitoring device is put into an opening validated mode of operation 13.

The term "validated by the final addressee" is used to mean that the final addressee uses the server and the external communications unit to indicate that opening of the container 2 is expected and does not correspond to a malfunction, or to a fraud, or to erroneous handling, etc.

When the monitoring device is in the warning mode of operation 12 and the communications module receives an acknowledgment message indicating that an open message has been received, the monitoring device is put into a reception validated mode of operation 14. The reception of an acknowledgment message means that the external communications unit is indeed receiving the messages transmitted by the communications module (or at least some of them).

In the opening validated mode of operation 13, the detection means detect whether the container 2 is open or closed, the sensors measure the internal electrical parameters of the monitoring device, and the communications module sends a third number of status messages at a third status repetition rate.

The third status repetition rate is lower than the second status repetition rate and higher than the first status repetition rate, and in this example it is equal to sending once every thousand seconds.

The third number of status messages is lower than the second number of status messages and it is higher than the first number of status messages.

The status messages comprise open messages meaning that the detection means detect that the container 2 is open.

The communications module also sends a third number of supervision messages at a third supervision repetition rate, the supervision messages comprising the internal electrical parameters of the monitoring device for the purpose of monitoring that it is operating correctly.

If the detection means detect that the container 2 is closed, the monitoring device is put into the closed mode of operation 11.

In the reception validated mode of operation 14, the reception means detect whether the container 2 is open or closed, the sensors measure the internal electrical parameters of the monitoring device, and the communications module sends a fourth number of status messages at a fourth status repetition rate.

The fourth status repetition rate is lower than the second status repetition rate and higher than the third status repetition rate.

The fourth status repetition rate in this example is equal to sending once every hundred seconds.

The fourth number of status messages is lower than the second number of status messages and higher than the third number of status messages.

The status messages comprise open messages indicating that the detection means detect that the container 2 is open.

The communications module also sends a fourth number of supervision messages at a fourth supervision repetition rate, the supervision messages comprising the internal electrical parameters of the monitoring device.

The communications module also "listens" to the LPWAN network by activating the transceiver to receive at a second reception repetition rate.

If the detection means detect that the container 2 is closed, the monitoring device is put into the closed mode of operation 11.

If the communications means receive an opening validated message meaning that opening of the container has been validated by the final addressee, the monitoring device is put into the opening validated mode of operation 13.

The warning mode of operation 12, the opening validated mode of operation 13, and the reception validated mode of operation 14 thus enable the status repetition rate and the number of status messages that are sent to be adapted as a function of receiving acknowledgment messages and opening validated messages.

In the warning mode of operation 12, the second status repetition rate and the second number of status messages are thus large in order to maximize the chances of reception. Specifically, in the warning mode of operation 12, it is not known whether the detected opening is normal opening or suspect opening, and it is not even known whether the messages sent by the communications module are being received properly.

Once an acknowledgment message has been received, communication with the external communications unit is established. The monitoring device is then in the reception validated mode 14, and thus the fourth status repetition rate and the fourth number of status messages in the reception validated mode of operation 14 can be reduced.

Likewise, once an opening validated message has been received, frequent monitoring is no longer necessary, since not only has opening of the container 2 been properly detected by the detection means, but it has also been validated by the final addressee. The monitoring device is then in the opening validated mode 13 and the third status repetition rate and the third number of status messages of the reception validated mode of operation can be further reduced.

Finally, when no opening is detected, monitoring is reduced as much as possible. The monitoring device is then in the closed mode 11, and the first status repetition rate and the first number of status messages in the reception validated mode of operation are very low.

Naturally, this applies likewise for the supervision repetition rates and for the number of supervision messages.

As mentioned above, when the monitoring device is not activated for performing the functions of detection, measurement, sending a message, or receiving a message, the monitoring device is in a low-consumption standby mode 10.

Thus, by reducing the repetition rate and the number of messages whenever a high repetition rate and a large number of messages are not required, the electricity consumption of the monitoring device is reduced, so the length of time the monitoring device can operate is increased, and may amount to several years when using a standard battery.

Figure 3:
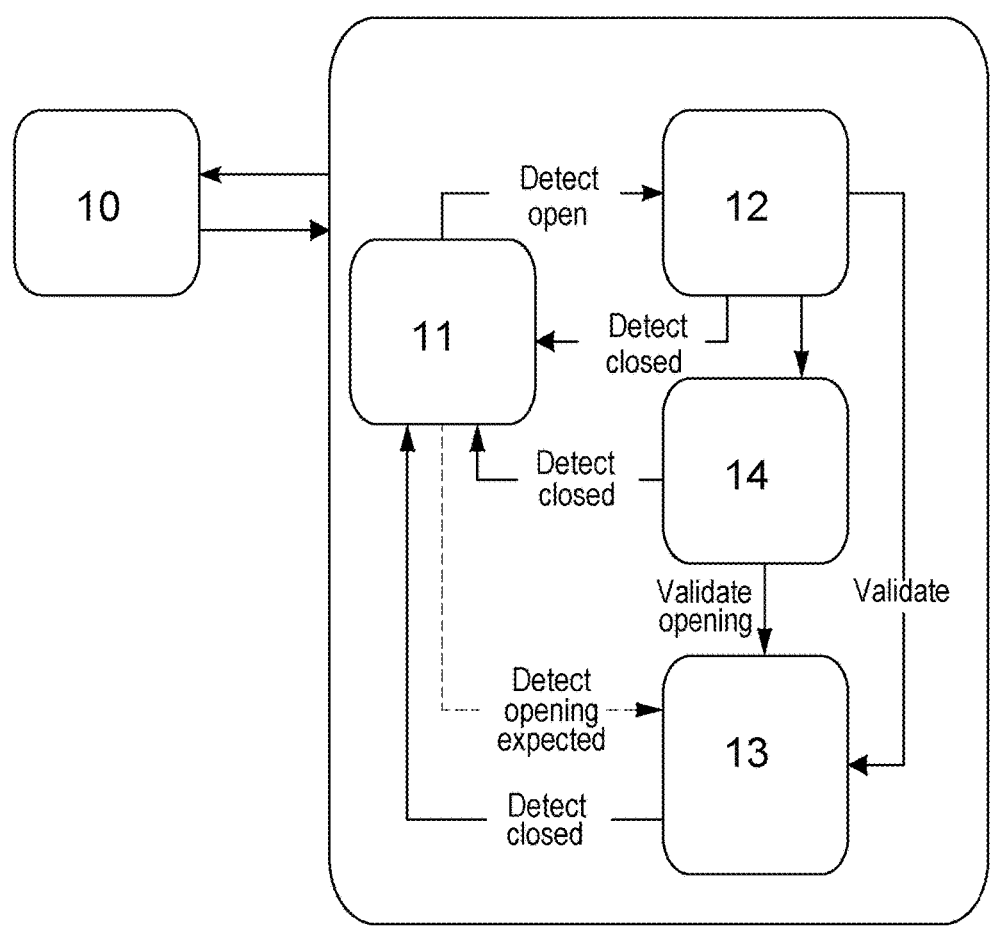
FIG. 3 is a diagram showing the operation of the monitoring method in a second implementation of the invention.

The monitoring method in a second implementation of the invention is described with reference to FIG. 3.

The monitoring method in the second implementation of the invention differs from the first implementation only by including the following improvements.

In the second implementation, while the monitoring device is in the closed mode of operation 11, the communications module also "listens" to the LPWAN network by activating the transceiver to receive at a third reception repetition rate.

The communications module can then receive an opening expected message coming from the final addressee.

The opening expected message means firstly that the final addressee expects that the container will be open in the short term by some person, e.g. an operator. The opening expected message also means that the final addressee authorizes such opening.

When an opening expected message is received by the communications module, the monitoring device is put into the opening validated mode of operation 13.

The operator can then open the container and access its contents inside the container.

It should be observed that the third reception repetition rate is relatively low, e.g. corresponding to activating the transceiver to receive once per day.

It should also be observed that the third reception repetition rate is adjustable, in particular as a function of the probability that an opening expected message is going to be received. The duration for which reception is activated is also adjustable.

Naturally, the invention is not limited to the implementations described but covers any variants coming within the ambit of the invention as defined by the claims.

By way of example, it is possible to make provision for the modes of operation to be slightly different, e.g. for the supervision messages to be different, or indeed for them to be sent only during certain modes of operation, or indeed for them to contain the remaining capacity of the battery, etc.

Although it is mentioned only that the third reception repetition rate is adjustable, all of the above-mentioned repetition rates are adjustable. Likewise, all of the durations for which the monitoring device is to perform the functions of detection, measurement, sending a message, or receiving a message are adjustable.

The invention claimed is:

1. A monitoring method for monitoring the opening of a container, the monitoring method being performed by a monitoring device comprising means for detecting opening and closing of the container and a communications module, the monitoring method comprising the steps of:

putting the monitoring device into a closed mode of operation when the detection means detect that the container is closed, in which mode the communications module sends closed messages at a first status repetition rate, the closed messages indicating that the detection means detect that the container is closed;

when the monitoring device is in the closed mode of operation and the detection means detect that the container is open, putting the monitoring device into a warning mode of operation in which the communications module sends open messages at a second status repetition rate, the open messages indicating that the detection means detect that the container is open; and when the monitoring device is in the warning mode of operation and the communications module receives an opening validated message indicating that opening of the container has been validated, putting the monitoring device in an opening validated mode of operation in which the communications module sends open messages at a third status repetition rate, the open messages indicating that the detection means detect that the container is open.

2. A monitoring method according to claim 1, wherein the second status repetition rate is higher than the third status repetition rate, which is higher than the first status repetition rate.

3. A monitoring method according to claim 1, wherein, when the monitoring device is in the warning mode of operation, and the communications module receives an acknowledgment message indicating that an open message has been properly received, the monitoring device is put into a reception validated mode of operation in which the communications module sends an open message at a fourth status repetition rate indicating that the detection means detect that the container is open.

4. A monitoring method according to claim 3, wherein, when the monitoring device is in the reception validated mode of operation and the communications module receives the opening validated message, the monitoring device is put into the opening validated mode of operation.

5. A monitoring method according to claim 3, wherein the fourth status repetition rate is lower than the second status repetition rate and higher than the third status repetition rate.

6. A monitoring method according to claim 1, wherein, when the monitoring device is in the closed mode of operation and the communications module receives an opening expected message indicating that opening of the container is expected and authorized, the monitoring device is put into the opening validated mode of operation.

7. A monitoring method according to claim 3, wherein a supervision message relating to proper operation of the monitoring device is sent at a first supervision repetition rate when the monitoring device is in the closed mode of operation, and/or at a second supervision repetition rate when the monitoring device is in the warning mode of operation, and/or at a third supervision repetition rate when the monitoring device is in the opening validated mode of operation, and/or at a fourth supervision repetition rate when the monitoring device is in the reception validated mode of operation.

* * * * *